United States Patent [19]

Witt

[11] Patent Number: 4,842,585
[45] Date of Patent: Jun. 27, 1989

[54] STEEL CANNULA FOR SPINAL AND PERIDURAL ANAESTHESIA

[75] Inventor: Hans-Hinrich Witt, Körle, Fed. Rep. of Germany

[73] Assignee: B. Braun Melsungen AG, Melsungen, Fed. Rep. of Germany

[21] Appl. No.: 129,643

[22] Filed: Dec. 7, 1987

[30] Foreign Application Priority Data

Dec. 18, 1986 [DE] Fed. Rep. of Germany ....... 3643235

[51] Int. Cl.$^4$ .............................................. A61M 5/00
[52] U.S. Cl. .................................... 604/158; 604/274
[58] Field of Search ................................. 604/51–53, 604/158–170, 272–274

[56] References Cited

U.S. PATENT DOCUMENTS

| | | | |
|---|---|---|---|
| 2,634,726 | 4/1953 | Hanson | 604/274 |
| 2,922,420 | 1/1960 | Cheng | 604/158 X |
| 4,413,993 | 11/1983 | Guttman | 604/274 |
| 4,552,554 | 11/1985 | Gould et al. | 604/104 X |
| 4,645,491 | 2/1987 | Evans | 604/158 |

FOREIGN PATENT DOCUMENTS

| | | | |
|---|---|---|---|
| 3020926 | 12/1981 | Fed. Rep. of Germany | 604/274 |
| 624618 | 9/1978 | U.S.S.R. | 604/160 |

*Primary Examiner*—Dalton L. Truluck
*Attorney, Agent, or Firm*—Spensley Horn Jubas & Lubitz

[57] ABSTRACT

The front end of the guide channel of a steel cannula is provided with an oblique guide surface adapted to direct an inserted catheter to the outside in order to project out of the tube. The ground surface surrounding the opening is of funnel wall design. Due to the steel cannula, a catheter may be applied by means of a simple cannula without the probable risk of being cut or damaged.

4 Claims, 1 Drawing Sheet

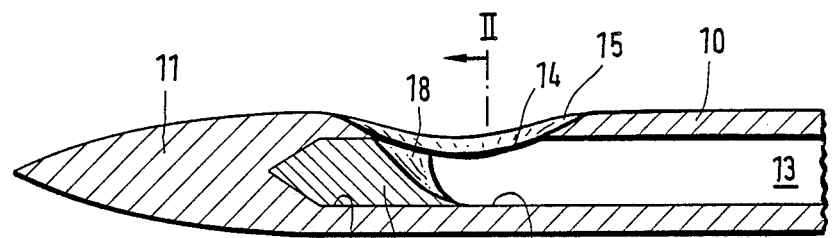
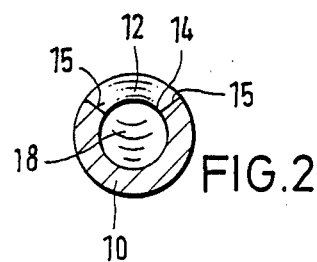
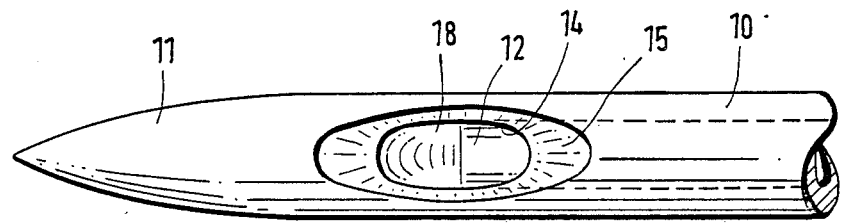
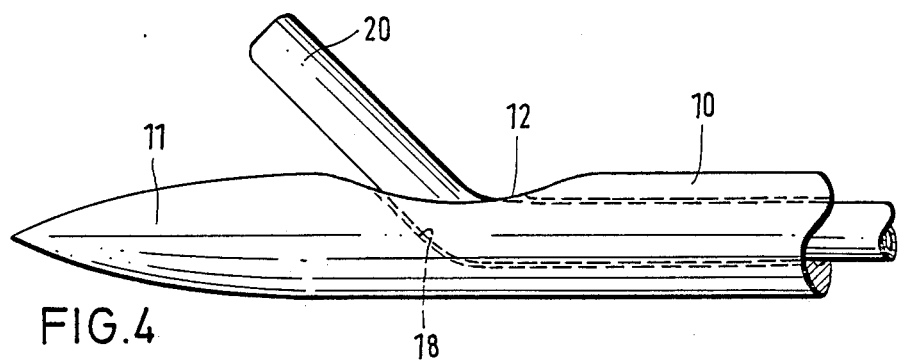

STEEL CANNULA FOR SPINAL AND PERIDURAL ANAESTHESIA

BACKGROUND OF THE INVENTION

1. Field of the Invention

The present invention relates to a steel cannula for spinal and peridural anaesthesia, and in particular a steel cannula comprising a straight tube whose front end includes an atraumatically pointed rotationally symmetric tip and an elongated lateral opening of the tube channel provided behind the tip.

2. Description of Related Art

The use of cannulas having a ground surface with a cutting or tearing property may be accompanied by injuries of vessels, dura and nerves in the case of spinal or peridural anaesthesia. Above all, bleeding in the peridural space, postspinal headaches and temporary to persistent neuronal losses of function may occur.

A known steel cannula for spinal and peridural anaesthesia consists of a rectilinear tube having a pointed front end. Immediately behind the top portion, a lateral elongated opening is ground into the cannula wall to extend as far as possible to the center axis of the cannula and to merge edgelessly with its front and rear border into the top portion or the external jacket surface of the cannula. The tube channel extends beyond the front end of the opening as far as into the top portion. Such a steel cannula causes a slight atraumatic puncture hole, because the point separates the longitudinal fibers of the dura and it does not cut through them. Such a steel cannula is not suitable for positioning a catheter, but only for directly injecting anaesthetic through the cannula channel. As compared to the rigid steel cannula, a flexible catheter is more advantageous for injecting anesthetics and drugs because of its longer service life. Moreover, it may be left in the body upon the removal of the cannula used for its application.

There has also been known a double cannula (German OS No. 32 18 242) having a sharp open point and an inner cannula whose blunt tip is closed and round. From an opening provided laterally behind the blunt tip, a catheter which is introduced through the inner cannula is adapted to be guided out through an oblique guide surface. The disadvantages involved with said double cannula reside in the great expenditure concerning puncture cannula and inner cannula, the complicated techniques for applying the catheter, and the intensive bleeding in the epidural space caused by the blunt tip.

It is an object of the present invention to provide a one-piece cannula which may be applied in one move and which is adapted to safely position a catheter.

SUMMARY OF THE INVENTION

In accordance with the present invention, these and other objects are achieved by providing a steel cannula having a tube channel which ends at a guide surface. The guide surface ascends obliquely from the bottom of the tube channel towards the end of an opening. A catheter is provided which is displaceable in the tube channel. The front end of the catheter is supported by a guide surface and may exit the tube laterally.

The steel cannula of the present invention which, by means of its atraumatically pointed tip may directly puncture the dura without injuring its fibers, not only allows the direct injection of liquids, but also allows the application of a catheter. During its application, the catheter is advanced in the tube channel. If the catheter front end arrives at the guide surface, it is deviated laterally and obliquely in the forward direction so that the catheter is prevented from getting within reach of the sharp end of the cannula tip. Therefore, the cannula may be withdrawn without entailing the risk of damaging or cutting off the catheter by the cannula tip. Since the catheter top is not traumatically blunt, its advance in the peridural space does not cause pain for the patient. The atraumatic top penetrates the tissue and the skin of the nerves without a cutting effect or a substantial impact. On the contrary, the material to be penetrated is carefully moved apart and closed again upon the removal of the steel cannula provided for a single-shot application. In other words, it is advanced in one move as far as the peridural space.

In the case of the steel cannula of the present invention, the lateral opening is not ground as far as into the range of the center axis thereof. The width of the elongated opening is substantially equal to the diameter of the tube channel. The ground surface enclosing the opening forms an elongated funnel whose wall is universally inclined towards the opening border so that the outer contour of the steel cannula is modified as little as possible within the range of the opening. The sharp-edged opening borders are recessed relative to the outer contour, thus excluding any cutting action when the steel cannula is advanced or withdrawn.

BRIEF DESCRIPTION OF THE DRAWINGS

An embodiment of the invention will be explained hereunder in more detail with reference to the drawings in which FIG. 1 is a longitudinal section of the steel cannula, FIG. 2 is a cross section along line II—II of FIG. 1, FIG. 3 is a plan view of the steel cannula during the introduction of a catheter, FIG. 4 is a side view of the steel cannula during the introduction of a catheter.

DESCRIPTION OF THE PREFERRED EMBODIMENT

The following detailed description is of the best presently contemplated mode of carrying out the invention. This description is not to be taken in a limiting sense, but is made merely for the purpose of illustrating the general principle of the invention. The scope of the invention is defined by the appended claims.

The illustrated steel cannula comprises an elongated straight tube 10 whose front end is closed by a rotationally symmetric tip 11 formed integrally with tube 10, said tip 11 being at least twice as long as the dimension of the outer diameter of tube 10, preferably about 2.5 times its size. The external surface of the rotationally symmetric tip 11 is slightly spherical, the transition to the outer surface of the tube 10 being continuous or kinkless.

Behind tip 11 and slightly spaced therefrom, an elongated lateral opening 12 of an elliptic shape is provided in tube 10, the main axis of said opening extending in parallel to the tube axis. Opening 12, which directly communicates with tube channel 13, is confined by border 14 which, at the same time, forms the inner boundary of a ground surface 15 circumadjacently enclosing the opening 12. Surface 15 is a funnel wall universally inclined towards the border 14. In each cross section of the tube, the two confronted areas of surface 15 extend at an angle with respect to each other (FIG. 2). In other words, the confronted surface areas 15 are not situated in a common plane. As a result thereof, each point of the external border of the ground surface 15 is higher than the border 14 of the opening 12. While the border 14 extends relatively close to the vicinity of the longitudinal central plane of the tube 10 (which plane is parallel to opening 14), the distance of the external edge of surface 15 is farther away from said plane.

Tube channel 13 is elongated by a lengthening piece 16 projecting beyond opening 12. Tube channel 13 is filled by a plug 17 of soldering material, plastic, or the like, so that the end of the clear tube channel is defined by plug 17. The rear end of plug 17 is designed as a guide surface 18 which ascends continuously forwardly and laterally towards border 14 from the bottom 19 of the tube channel 13, i.e. from the inner surface averted from the opening 12.

With reference to the tube channel, said guide surface 18 is shaped convexly. In other words, it is deflected towards plug 17. Further, the guide surface 18 is bent in transverse direction of the tube 10 in accordance with the extent of the border 14 at the front end of the opening 12. The upper end of the guide surface 18 is directly adjoined to the border 14. Due to the guide surface, a catheter 20 being advanced through the tube 10 may be laterally guided out of the opening 12 so that the catheter end projects obliquely in the forward direction from the tube 10, such as illustrated in FIG. 4. In said position, the tube 10 may be withdrawn while, due to the guide surface 18, the catheter 20 which maintains its position is pressed laterally out of the tube.

In a manner known per se, the catheter 20 consist of a flexible tube, its diameter being inferior to that of the tube channel 13, thus facilitating the advance of the catheter in the tube channel. Since, in the transverse direction, the diameter of the opening is slightly superior to that of the tube channel 13, the catheter 20 may easily slip through the opening 14. The border 14 at the rear end of the elongated opening 12 should be as blunt as possible to ensure that it does not cut the catheter 10 when it is removed.

The maximum length of the opening 14 is twice its width so that the catheter fits snugly and is moved steeply out of the steel cannula in the direction of the guide surface 18.

The presently disclosed embodiments are to be considered in all respects as illustrated and not restrictive, the scope of the invention being indicated by the appended claims, rather than the foregoing description, and all changes which come within the meaning, the range of the equivalency of the claims are therefore intended to be embraced therein.

What is claimed is:

1. A steel cannula for spinal and peridural anaesthesia, comprising:
   a substantially straight tube having a tube channel therein, the tube terminating in an atraumatically pointed, rotationally symmetric tip, the tube having an elongated lateral opening therein provided behind the tip, the opening extending to the tube channel and having a border therearound,
   a guide surface extending from the bottom of the tube channel and ascending obliquely towards the end of the opening,
   a ground surface enclosing the opening, the ground surface forming an elongated funnel whose wall is universally inclined towards the border of the opening, and
   a catheter displaceably positioned in the tube channel, the catheter having a front end supported by the guide surface,
   whereby the guide surface urges the catheter to exit the tube laterally.

2. A steel cannula as defined in claim 1, further comprising a plug disposed in the tube channel, the guide surface being coextensive with at least a portion of the surface of the plug.

3. A steel cannula as defined in claim 1, wherein the guide surface is substantially parallel to the border of the opening.

4. A steel cannula as defined in claim 1, wherein the tip is at least twice as long as the external diameter of the tube.

* * * * *